(12) United States Patent
Itozaki

(10) Patent No.: US 9,377,398 B2
(45) Date of Patent: Jun. 28, 2016

(54) LIQUID INSPECTING METHOD AND LIQUID INSPECTING DEVICE

(75) Inventor: Hideo Itozaki, Suita (JP)

(73) Assignee: OSAKA UNIVERSITY, Suita-Shi (JP)

( * ) Notice: Subject to any disclaimer, the term of this patent is extended or adjusted under 35 U.S.C. 154(b) by 939 days.

(21) Appl. No.: 13/122,458

(22) PCT Filed: Oct. 2, 2009

(86) PCT No.: PCT/JP2009/067263
§ 371 (c)(1),
(2), (4) Date: Apr. 4, 2011

(87) PCT Pub. No.: WO2010/041608
PCT Pub. Date: Apr. 15, 2010

(65) Prior Publication Data
US 2011/0186738 A1    Aug. 4, 2011

(30) Foreign Application Priority Data

Oct. 6, 2008   (JP) ................................. 2008-259789

(51) Int. Cl.
*G01J 5/02*    (2006.01)
*G01N 21/359*  (2014.01)
(Continued)

(52) U.S. Cl.
CPC .......... *G01N 21/359* (2013.01); *G01N 21/3577* (2013.01); *G01N 21/9027* (2013.01); *G01N 33/22* (2013.01)

(58) Field of Classification Search
CPC ............ G01N 21/3577; G01N 21/359; G01N 15/205; G01N 21/90
USPC ........................................ 250/339.12, 339.11
See application file for complete search history.

(56) References Cited

U.S. PATENT DOCUMENTS 4,368,980 A  *  1/1983  Aldred et al. .............. 356/239.4
5,349,189 A      9/1994  Maggard
(Continued)

FOREIGN PATENT DOCUMENTS

EP    0 714 024 A1    5/1996
EP    2071320 A1      6/2009
(Continued)

OTHER PUBLICATIONS

Chinese Office Action, dated Sep. 24, 2012, for Chinese Application No. 200980138922.6.
(Continued)

*Primary Examiner* — David J Makiya
*Assistant Examiner* — Kenneth J Malkowski
(74) *Attorney, Agent, or Firm* — Birch, Stewart, Kolasch & Birch, LLP

(57) ABSTRACT

A liquid inspecting method, for inspecting the situation of containing explosives, explosive materials and/or illegal drugs in liquid filled in a light transmitting container, comprises a step for irradiating the liquid with near-infrared light from the outside of the container, a step for receiving near-infrared light transmitted through the liquid or scattered by the liquid, and a step for analyzing the absorption spectrum of received near-infrared light. The situation of containing explosives, explosive materials or illegal drugs in liquid filled in a light transmitting container such as a PET bottle or a glass bottle can be detected quickly and certainly from the outside of the container by providing a liquid inspecting method for analyzing the absorption spectrum, and a liquid inspecting device for use therein.

15 Claims, 4 Drawing Sheets

(51) Int. Cl.
  *G01N 21/3577* (2014.01)
  *G01N 21/90* (2006.01)
  *G01N 33/22* (2006.01)

(56) References Cited

U.S. PATENT DOCUMENTS

| | | | |
|---|---|---|---|
| 5,708,273 | A | 1/1998 | VonBargen |
| 6,339,222 | B1 | 1/2002 | Kester et al. |
| 6,707,556 | B2 * | 3/2004 | Turner et al. ............ 356/436 |
| 2002/0084416 | A1 * | 7/2002 | Kiuchi ................. 250/339.12 |
| 2003/0174326 | A1 * | 9/2003 | Rzasa et al. ............ 356/326 |
| 2004/0000653 | A1 * | 1/2004 | Nordlund ................ 250/573 |
| 2009/0146061 | A1 | 6/2009 | Manneschi |

FOREIGN PATENT DOCUMENTS

| | | |
|---|---|---|
| GB | 2297377 A | 7/1996 |
| JP | 8-145881 A | 6/1996 |
| JP | 10-48129 A | 2/1998 |
| JP | 10-54761 A | 2/1998 |
| JP | 11-51928 A | 2/1999 |
| JP | 2000-131228 A | 5/2000 |
| JP | 2003-121352 A | 4/2003 |
| JP | 2004-163369 A | 6/2004 |
| JP | 2006-266948 A | 10/2006 |
| WO | WO 2008/034232 A1 | 3/2008 |

OTHER PUBLICATIONS

Wu et al., "Research on Shortwave NIR Spectroscopy and Its Application to in Situ Flammable Liquid Detection", Spectroscopy and Spectral Analysis, Sep. 2008, vol. 28, No. 9, pp. 2087-2089.

Cho et al., "Determination of Water Content in Ethanol by Miniaturized Near-Infrared (NIR) System," Bull. Korean Chem. Soc., vol. 26, No. 1, 2005, pp. 115-118.

Eliasson et al., "Noninvasive Detection of Concealed Liquid Explosives Using Raman Spectroscopy," Anal. Chem., 2007, vol. 79, No. 21, pp. 8185-8189.

International Search Report and Written Opinion (including Forms PCT/IPEA/409 and PCT/ISA/237 and PCT/IB/338) in PCT/JP2009/067263 mailed Nov. 10, 2009.

Lee et al., "Improving the robustness of a partial least squares (PLS) model based on pure component selectivity analysis and range optimization: Case study for the analysis of an etching solution containing hydrogen peroxide," Analytica Chimica Acta, vol. 572, 2006, pp. 93-101.

The official website of Tokyo Gas Co., Ltd. and Tokyo Gas Engineering Co., Ltd., online information entitled: "Launch of Intra-Bottle Liquid Inspection Device SLC-211D," Nov. 1, 2004 (retrieved on Sep. 22, 2008 URL: http://www.tokyo-gas.co.jp/Press/20041101/html).

Woo et al., "Determination of hydrogen peroxide concentration in antiseptic solutions using portable near-infrared system," Journal of Pharmaceutical and Biomedical Analysis, vol. 33, 2003, pp. 1049-1057.

Yoshida, "Kasairui no kinsekigabunkouhou ni yoru hihakai sokuteihou no kaihatsu meron no toudo sokuteino tameno kanni bunseki syuhou no kentou," JUSE Communication, 2008, pp. 1-5, including a partial English translation.

Burrows et al., "Screening of Bottles," Security and Detection, European Convention on Brighton, UK, Jan. 1, 1995, pp. 115-119.

The Communication and Extended European Search Report, dated Mar. 18, 2014, issued in the corresponding European Patent Application No. 09819143.0.

The Second Office Action (including an English translation), dated Jun. 4, 2013, issued in the corresponding Chinese Patent Application No. 200980138922.6.

The Third Office Action (including an English translation), dated Dec. 17, 2013, issued in the corresponding Chinese Patent Application No. 200980138922.6.

The Fourth Office Action (including an English translation), dated Jun. 23, 2014, issued in the corresponding Chinese Patent Application No. 200980138922.6.

* cited by examiner (a)

(b)

LIQUID INSPECTING METHOD AND LIQUID INSPECTING DEVICE

TECHNICAL FIELD

The present invention relates to a method for inspecting a liquid with which an optically transparent container is filled and to a liquid inspection device. More particularly, the present invention relates to an inspection method and an inspection device for checking whether an explosive, a raw material for explosive, or an illicit drug of some kind is contained in a liquid with which an optically transparent container is filled.

BACKGROUND ART

Including the simultaneous terrorist bomb explosion incidents that occurred in Great Britain in 2005, terrorist bomb explosion incidents have occurred frequently at public facilities and public transportation in recent years. In recent times, there have been growing cases where a dangerous character, such as a terrorist, pretending to be a passenger carries onto an airplane or the like an optically transparent container for a drink, such as a PET bottle, or a glass bottle, for example, filled with a liquid in which an explosive, a raw material for explosive, or the like has been mixed or dissolved. Further, there have also been growing cases where a liquid, in which an illicit drug such as a narcotic or a stimulant has been dissolved, is smuggled in a manner that an optically transparent container is filled with the illicit drug.

As measures against the carrying of explosives, a raw material for explosive, and illicit drugs on airplanes, hand luggage inspections are conducted on passengers at airports for preventing occurrence of incidents such as terrorist incidents, and smuggling. In order to conduct inspections on many passengers, there is a need to swiftly conduct the inspections, but it is not easy to determine whether or not a liquid with which a container has been filled contains an explosive, a raw material for explosive, or an illicit drug during short-time inspection.

As a method for inspecting a liquid from outside a container without opening the container under such circumstances, a detection method has already been proposed which is used to swiftly determine whether a liquid is a combustible liquid, such as gasoline, or not (see Non-Patent Document 1). In such a detection method, the determination whether a liquid is a dangerous substance or not is made based on a fact that water, the main ingredient in a regular drink is different in permittivity from combustibles such as gasoline, specifically based on a fact that water is higher in permittivity than gasoline.

However, there have been growing cases where a dangerous substance close to water in permittivity is used in recent times; for example, in the foregoing incident that occurred in Great Britain, a mixed solution of hydrogen peroxide and acetone was used as an explosive. Therefore, as to detection of dangerous liquid substance close to water in permittivity, the detection method described in Non-Patent Document 1 is not an effective detection method.

On the other hand, in the USA, a device is commercially available which is capable of detecting a hydrogen peroxide solution from outside an optically transparent container by means of Raman spectroscopy. However, in the case where Raman spectroscopy is used, since optically transparent containers and liquids in the containers show strong fluorescence, necessary detection sensitivity can be hardly obtained; therefore the fact is that the device is scarcely in practical use.

PRIOR ART DOCUMENT

Non-Patent Document

Non-Patent Document 1: the official website of Tokyo Gas Co., Ltd. and Tokyo Gas Engineering Co., Ltd., online information entitled "Launch of Intra-Bottle Liquid Inspection Device SLC-211D", Nov. 1, 2004 (retrieved on Sep. 22, 2008 URL:http://www.tokyo-gas.co.jp/Press/20041101/html)

SUMMARY OF THE INVENTION

Problems to be Solved by the Invention

In airplanes etc. that are particularly important as public carriers among public facilities and public transportation where there is a need to take antiterrorism measures, the fact is that carrying-in of drinking water and so forth is prohibited at present because there is no suitable method for detecting various explosives, raw materials for explosives, illicit drugs, and so on in a short time as described above.

Therefore, it is an object of the present invention to provide an inspection method and an inspection device in which whether an explosive, a raw material for explosive, or an illicit drug of some kind is contained in a liquid with which an optically transparent container, such as a PET bottle or a glass bottle, is filled can be checked swiftly and reliably from outside the container.

Means of Solving the Problems

The present inventors conducted extensive studies in order to solve the above problems. As a result, it was found that the above problems can be solved by inventions of the Claims shown below, and thus the present invention has been completed.

The invention of Claim 1 is
a liquid inspection method for checking whether an explosive, a raw material for explosive, or an illicit drug is contained in a liquid with which an optically transparent container is filled, comprising:
a near-infrared irradiation step in which the liquid is irradiated with near-infrared light from outside the container;
a near-infrared light reception step in which the near-infrared light passed through the liquid or the near-infrared light scattered by the liquid is received; and
an absorption spectrum analysis step in which an absorption spectrum of the received near-infrared light is analyzed, wherein whether an explosive, a raw material for explosive, or an illicit material is contained in a liquid with which the container is filled is checked by analyzing the absorption spectrum.

According to the invention of Claim 1, whether an explosive, a raw material for explosive, or an illicit drug (hereinafter collectively referred to as "dangerous substance") is contained in a liquid with which an optically transparent container, such as a PET bottle or a glass bottle, is filled can be checked swiftly and reliably without opening the container. In the following, the above checking method will be described in detail.

The present inventors carefully studied not only properties of the dangerous substances but also properties of liquids, such as drinks, and containers. As a result, it was found that whether a dangerous substance of some kind is contained can be checked swiftly and reliably by analyzing an absorption spectrum obtained by irradiating a container with near-infrared light from outside the container without opening the container.

Although water absorbs light well, it does not absorb near-infrared light much. Because of this, by irradiating a liquid containing a dangerous substance with near-infrared light and then analyzing the absorption spectrum thus obtained, whether a dangerous substance of some kind is contained or not can be checked. Further, unlike Raman spectroscopy, the use of near-infrared light does not present the problem of containers and liquids showing strong fluorescence which prevents sufficient detection sensitivity, and therefore makes it possible to obtain absorption spectra that can be analyzed sufficiently.

Moreover, even when a dangerous substance similar to water in properties, such as a hydrogen peroxide solution, is used, the dangerous substance can be detected correctly by devising a method for analyzing an obtained near-infrared light absorption spectrum.

Even when a liquid put in containers is water, tea, juice, cola, coffee, or the like, whether a dangerous substance of some kind is contained in the liquid can be checked readily by previously obtaining an absorption spectrum specific to the liquid. Further, the same goes for containers; that is, by previously obtaining absorption spectra specific to the containers, whether dangerous substances are contained in liquids can be checked readily irrespective of colors of the containers.

In the analysis of absorption spectra according to the invention, by suitably selecting several wavelengths from wavelengths of 650 to 1000 nm, the analysis can be conducted suitably. The selection of the specific wavelengths is carried out suitably in consideration of kinds of container, kinds of liquids to be put in the containers, and dangerous substances likely to be used.

Absorption spectra can be obtained by using either transmitted light or scattered light; it is preferable that scattered light be used because an irradiation unit and a light reception unit can be integrated into a single unit and the detection device can be, therefore, made compact.

As a light source for emitting near-infrared light, a white lamp can be preferably used. Further, as the irradiation direction when near-infrared irradiation is conducted from outside the container, any surface of the container may be irradiated provided that the surface is optically transparent. Undersurfaces of PET bottles and soon often have shapes suitable for light scattering, and thus it is preferable that the irradiation be conducted from the direction of the undersurfaces.

At the time of the near-infrared light irradiation, in order to avert an adverse effect of extraneous light, it is preferable to shield the whole container from extraneous light.

The invention of Claim 2 is the liquid inspection method according to Claim 1, wherein identification of the kinds of the explosive, raw material for explosive, and/or illicit drug is conducted by analyzing the absorption spectrum.

According to the invention of Claim 2, kinds of the dangerous substances are identified, whereby dangers posed by the dangerous substances can be detected swiftly, and appropriate measures can be taken against the dangers.

The invention of Claim 3 is the liquid inspection method according to Claim 1 or Claim 2, wherein absorbance at the predetermined wavelengths of an absorption spectrum analyzed at the absorption spectrum analysis step is substituted into a concentration estimation equation formulated based on absorption spectra analyzed by using a plurality of liquids that contain the explosive, the raw material for explosive, and/or the illicit drug with preset concentrations to measure a concentration of the explosive, the raw material for explosive, and/or the illicit drug.

According to the invention of Claim 3, the concentration of the dangerous substance is measured and the level of danger can be clearly determined. And further, since the absorbance at the predetermined wavelengths of the analyzed absorption spectra is merely substituted into the concentration estimation equation formulated based on the absorption spectra analyzed by using the solutions containing the dangerous substances with the preset concentrations, the concentration can be measured swiftly and readily.

The invention of Claim 4 is the liquid inspection method according to Claim 3, wherein the concentration estimation equation is formulated by conducting multiple regression analyses by using the absorbances at the wavelengths of the absorption spectra analyzed by using the liquids containing the explosive, the raw material for explosive, and/or the illicit drug with the preset concentrations.

In the invention of Claim 4, a more exact concentration estimation equation can be formulated by conducting the multiple regression analyses by using the absorbances at the wavelengths of the absorption spectra obtained by analysis of the liquids containing the dangerous substances with the preset concentrations. The use of the more exact concentration estimation equation makes it possible to accommodate subtle changes in the spectra, whereby the concentrations can be measured with higher accuracy.

In particular, it was found that when a dangerous substance close to water in properties is contained, it is very important to conduct multiple regression analysis in order to conduct accurate inspection.

The invention of Claim 5 is the liquid inspection method according to Claim 3 or 4, wherein an absorbance quadratic differential value at the predetermined wavelengths which is obtained by a quadratic differentiation for the absorption spectra is used as the absorbance.

In the invention of Claim 5, the use of the absorbance quadratic differential value determined by subjecting the absorption spectra quadratic differentiation makes it possible to clearly grasp subtle changes in the absorption spectra caused by the mixing of the dangerous substances. As a result, even more exact concentration estimation equation can be obtained.

The invention of Claim 6 is the liquid inspection method according to anyone of Claims 1-5, wherein the raw material for explosive is hydrogen peroxide.

Since hydrogen peroxide solutions are similar to water in physical, chemical, and optical properties, it is difficult to identify hydrogen peroxide solutions in a short time by conventional liquid inspection methods; therefore, hydrogen peroxide solution is easy to be carried in with filling in a drinking container. According to the present invention, hydrogen peroxide solutions can also be detected accurately, and thus it is possible to clearly show effects of the present invention.

The invention of Claim 7 is the liquid inspection method according to any one of Claims 3-6, wherein regular products are used as the liquids containing the explosive, the raw material for explosive, and/or the illicit drug with the preset concentrations, a concentration estimation equation is previously formulated for each of the regular products, a regular product corresponding to the inspection object is identified by reading the product labeling mark put on the inspection object, and the concentration of liquid explosive, raw material for explosive, and/or illicit drug in the inspection objects is measured by using the concentration estimation equation corresponding to the identified regular product.

According to the invention of this claim, concentrations of liquid explosive, raw material for explosive, illicit drug, and so on with which containers are filled can be measured with higher accuracy.

Containers and liquids to be inspected vary in kind. Containers are different in not only material (examples of containers include PET bottles, glass bottles, and colored glass bottles) but size and shape. As well, liquids vary in kind; examples of liquids include water, green tea, black tea, coffee, cola, and juice. Further, the absorption spectra differ depending on the materials for containers, the sizes and shapes of containers, and the kinds of liquids put in containers. Therefore, in measurement of concentrations using a typical concentration estimation equation so that the equation can be applied to various containers and liquids, there is a limit to accuracy of the measurement. In contrast, according to the invention of Claim 6, since a regular product corresponding to the inspection object is identified by reading a product labeling mark and then a concentration estimation equation specific to the identified regular product is used, a concentration of a dangerous substance in the inspection object can be measured with higher accuracy. Moreover, since a container and a liquid can be identified by using a simple method, i.e., by reading a product labeling mark, the effect of the present invention, i.e., the effect of being capable of swiftly conducting liquid inspection is not ruined.

The "product labeling mark" mentioned in Claim 7 refers to a bar code, or a QR code, for example.

The invention of Claim 8 is a liquid inspection device for inspecting whether an explosive, a raw material for explosive, or an illicit drug is contained in a liquid with which an optically transparent container is filled, comprising:

a near-infrared light irradiation mean for irradiating the liquid with near-infrared light from outside the container;

a near-infrared light reception mean for receiving the near-infrared light passed through the liquid or the near-infrared light scattered by the liquid; and an absorption spectrum analysis mean for analyzing an absorption spectrum of the received near-infrared light, wherein whether an explosive, a raw material for explosive, or an illicit drug is contained in the liquid with which the container is filled is inspected by analyzing the absorption spectrum.

The invention of Claim 8 is a device used for conducting the method of Claim 1. By an inspection conducted by using the liquid inspection device of Claim 8, whether a dangerous substance is contained in a liquid with which an optically transparent container, such as a PET bottle or a glass bottle, is filled can be inspected swiftly and reliably from outside the container without opening the container.

The invention of Claim 9 is the liquid inspection device according to Claim 8 wherein the near-infrared light irradiation mean and the near-infrared light reception mean are integrated.

According to the invention of Claim 9, since the near-infrared light irradiation mean and the near-infrared light reception mean are provided with both means integrated, a spacing between the near-infrared light irradiation unit and the near-infrared light reception unit is constant and absorption spectrum analysis can be, therefore, conducted accurately. In addition, by integrating both means, a compact liquid inspection device can be provided.

The invention of Claim 10 is the liquid inspection device according to Claim 8 or Claim 9, which further comprising a product labeling mark reading mean for reading a product labeling mark put on a regular product.

By using the device of the invention of Claim 10, the inspection method of invention of Claim 7 can be conducted. According to the invention of Claim 10, a liquid inspection device is provided which is capable of inspecting whether an explosive, a raw material for explosive, and/or an illicit drug are contained in the inspection object with higher accuracy.

Effects of the Invention

According to the present invention, an inspection method is provided in which whether an explosive, a raw material for explosive, or an illicit drug is contained in a liquid with which an optically transparent container, such as a PET bottle or a glass bottle, is filled can be inspected swiftly and reliably from outside the container; and an inspection device for the inspection method is provided.

MODE FOR CARRYING OUT THE INVENTION

An embodiment of the present invention will be described below. The invention is not limited to the embodiment described below. Note that various modifications can be made to the embodiment below within a scope that is the same as and equivalent to the scope of the invention.

1. A Configuration of a Liquid Inspection Device According to the Embodiment

Figure 1:
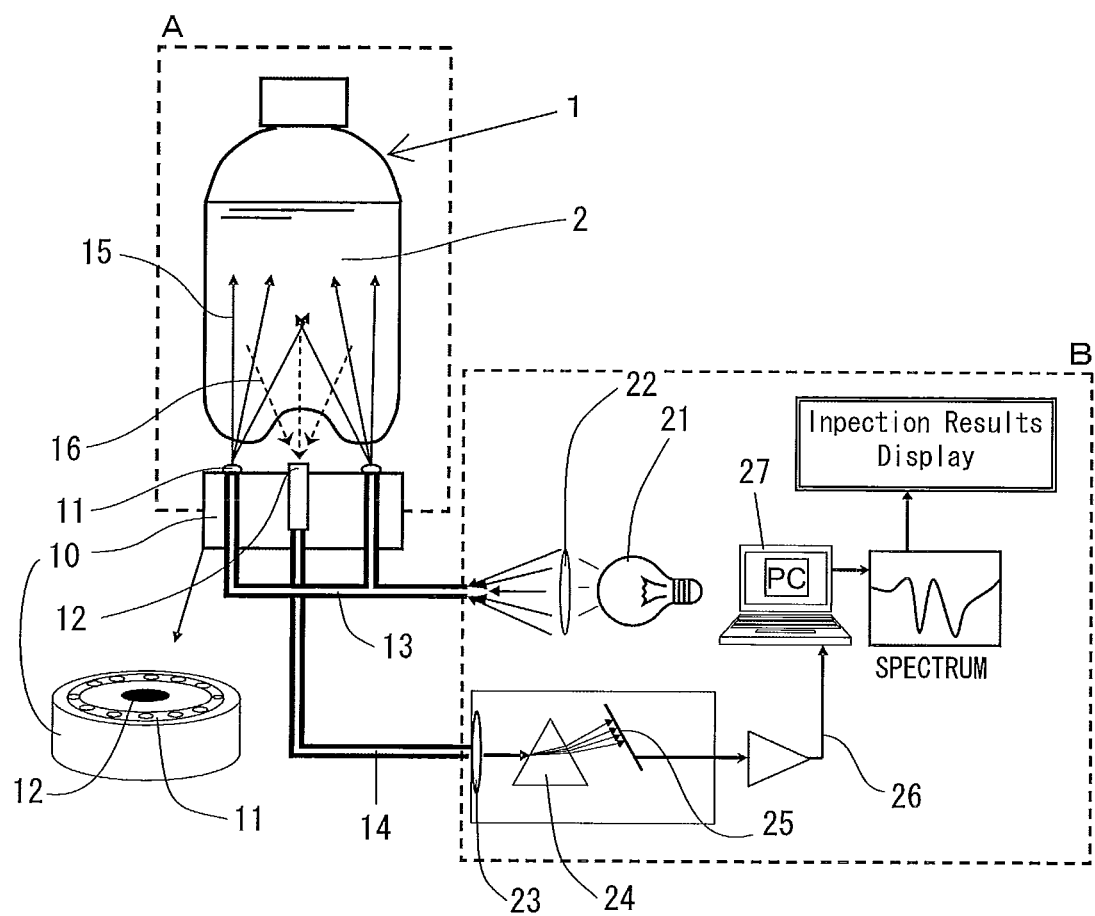
FIG. 1 is a schematic illustration of the main part of a liquid inspection device according to an embodiment of the invention.

At first, a configuration of a liquid inspection device according to the embodiment will now be described with reference to FIG. 1. FIG. 1 is an illustration schematically showing the main part of the liquid inspection device according to the embodiment. The main part is mainly constituted by a sample placement section A and an instrumentation section B. Both the section A and B are connected with each other by using optical fibers 13 and 14.

At the sample placement section A, a sensor head 10 is provided. The sensor head 10 comprises an irradiation unit 11 for near-infrared light irradiation and a light reception unit 12 to receive the near-infrared light. And further, on the sensor head 10, a container placement stage (not shown) is provided; on the placement stage, an optically transparent container 1 in which a liquid 2 is put is placed as a sample to be inspected. Top surface of a sensor head 10 may be used as a container placement stage.

At the instrumentation section B are provided a light source 21 to emit near-infrared light, lenses 22 and 23, a prism 24, and a personal computer (PC) 27 to analyze an absorption spectrum of the near-infrared light.

2. A Liquid Inspection Method According to the Embodiment

A Liquid put in a container is inspected for a dangerous substance by using the liquid inspection device having such a configuration as mentioned above according to the following procedure.

(1) Placement of Sample

Initially, the optically transparent container 1 filled with the liquid 2 is placed on the placement stage as a sample to be inspected. At that time, the container 1 is shielded from extraneous light by using a black cover or the like so that results of the inspection are not affected by the extraneous light.

(2) Near-Infrared Light Irradiation

Light emitted by turning on the light source 21 is concentrated by the lens 22, and then introduced into the irradiation unit 11 provided at the sensor head 10 through the optical fiber 13. Then the irradiation unit 11 irradiates the container 1 and the liquid 2 with near-infrared light 15. The applied near-infrared light 15 is scattered by the liquid 2, whereby scattered near-infrared light 16 is obtained.

(3) Reception of Scattered Near-Infrared Light

The scattered near-infrared light 16 is received by the light reception unit 12 provided at the sensor head 10, and then introduced into the prism 24 through the optical fiber 14 and the lens 23. At the prism, the near-infrared light is separated into its spectral components, and an absorption spectrum 25 can be obtained. Incidentally, it is preferable that an optical grating having a superior spectral analysis function be used instead of the prism 24.

Some of the near-infrared light 15 pass through the liquid 2 without being scattered. The light passed through the liquid 2 can also be subjected to analysis; in this case, a same process as the process described above can be executed by providing a light reception unit in a manner that opposes the light reception unit to an irradiation unit.

(4) Analysis of Absorption Spectrum

By substituting absorbance 26 at predetermined wavelength of the obtained absorption spectrum 25 into a concentration estimation equation preregistered in the PC 27, data on a dangerous substance in the liquid 2, such as the kind, concentration, etc. of the dangerous substance, is identified. Results of the inspection are communicated by PC 27, another display mean or a voice communication mean.

The above processes are registered in the PC as a program. Therefore, in an installation-type liquid inspection device, for example, containers can be inspected by merely placing the containers on a sensor head and irradiating the containers with near-infrared light.

Such a concentration estimation equation is formulated for each regular product; at the time of inspection of an inspection object in a container, a regular product corresponding to the inspection object is identified by reading a product labeling mark put on the container. Then the concentration estimation equation corresponding to the regular product is used to inspect the inspection object with higher accuracy.

3. Formulation of Concentration Estimation Equations

A basic procedure of the formulation of the concentration estimation equations will be described below.

(1) Obtaining Absorption Spectra

Absorption Spectra of near-infrared light differ depending on the kinds and concentrations of dangerous substances, the kinds of containers, and the kinds of liquids. Further, obtained absorption spectra also differ depending on not only combinations of those factors but quantities and temperatures of the liquids. Therefore, regarding dangerous substances likely to be used, a plurality of samples of each dangerous substance different in concentration are prepared in combination with various containers and liquids to obtain absorption spectra. Moreover, further absorption spectra are obtained by changing the quantity and temperature of each liquid.

(2) Formulation of Concentration Estimation Equations

Next, a concentration estimation equation, which shows relations between concentrations of a dangerous substance and absorbances at predetermined wavelengths of an absorption spectrum, is formulated by means of multiple regression analysis.

In particular, in the case where a dangerous substance close to water in properties, such as a hydrogen peroxide solution, is contained, it is difficult to interpret an absorption peak at the dangerous substance separately from an absorption peak at water. However, in the case where multiple regression analysis is performed, it becomes possible to grasp a subtle change in the absorption spectrum, whereby the inspection can be conducted with high accuracy.

Specifically, in multiple regression analysis, a following general equation (1), i.e., a multiple regression equation is set up which represents the relation between an estimated value of the concentration of a dangerous substance and the absorbance at the wavelengths, plurality of equations are formulated by substituting concentrations of liquids and absorbances at selected wavelengths ($\lambda_i$) of absorption spectra in Equation (1), and then a regression constant $\beta_0$ and biased regression coefficient $\beta_i$ in Equation (1) are determined by using a least squares method.

$$y = \beta_0 + \beta_1 x_1 + \beta_2 x_2 + \beta_3 x_3 + \ldots + \beta_p x_p \quad (1)$$

where x's are absorbances at the selected wavelengths $\lambda_i$ (i=1 to p), y is the concentration, $\beta_0$ is a regression constant (that depends upon quantity of a liquid, container, solution, etc.), and $\beta_i$'s are biased regression coefficients (that depends upon quantity of a liquid, container, solution, etc.).

Then, absorbances measured about liquid prepared separately which contains a preset concentration of dangerous substance are substituted in the multiple regression equation (1) in which the $\beta_0$ and the $\beta_i$ are determined to evaluate the multiple regression equation (1), and then a following equation (2), a concentration estimation equation, is finally formulated by making correction as necessary.

$$C = K_0 + K_1 E_1 + K_2 E_2 + K_3 E_3 + \ldots + K_p E_p \quad (2)$$

wherein c is a concentration (an estimated value), $E_n$s are absorbances at individual predetermined wavelengths, and $K_0$, $K_i$s are constants (from 1 to p).

By using absorbance quadratic differential values as the Es in the above concentration estimation equation instead of the absorbances, the subtle change in the spectrum can be grasped more accurately.

4. Concrete Examples of the Liquid Inspection Device According to the Invention

Figure 2:
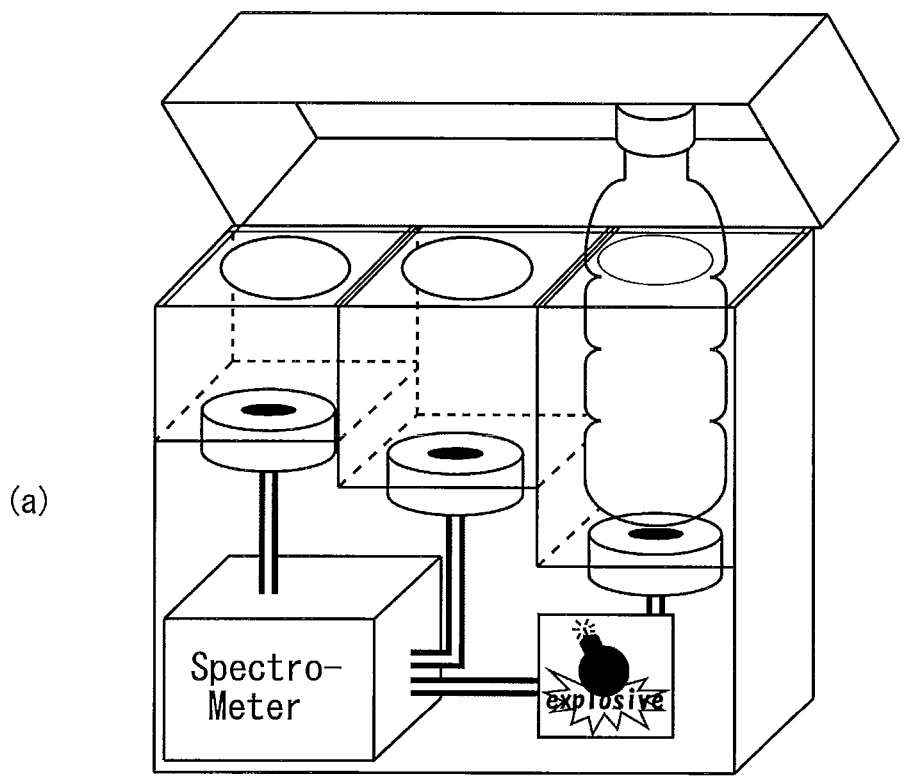
FIG. 2 is an illustration showing a concrete example of the liquid inspection device according to an embodiment of the invention.
Figure 2:
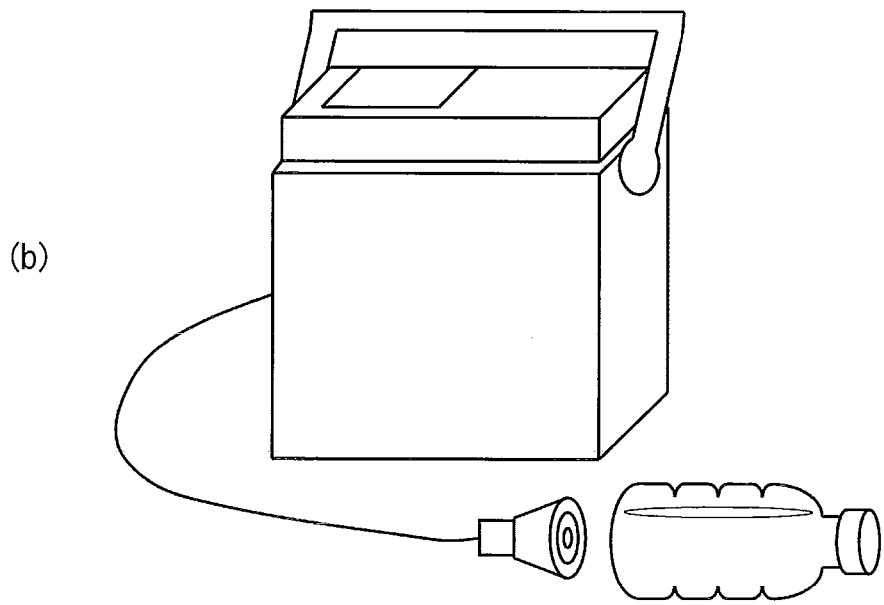

FIGS. 2(*a*) and 2(*b*) show concrete examples of the liquid inspection device according to the embodiment.

FIG. 2(*a*) is an illustration of an installation-type inspection device suitable for use in hand luggage inspection, in which plural sensor heads (in the figure, three sensor heads) are provided at heights different from each other. Therefore the inspection device is singly capable of inspecting containers different in size. Further, by closing a top lid, influence of extraneous light can be averted.

FIG. 2(b) is an illustration of a portable inspection device; by providing a sensor head outside the device, the inspection device is made compact. Further, since the sensor head is provided and separated from the body of the inspection device, near-infrared light irradiation can be performed in any direction. For example, discarded PET bottles and so on can be inspected from a place some distance from those inspection objects.

The present invention will be described in more detail below in accordance with following examples. In the following examples, an installation-type liquid inspection device using FTIR was used.

EXAMPLE 1

This is an example of measurement of concentration of hydrogen peroxide contained in aqueous hydrogen peroxide ($H_2O_2$) solutions with which various PET bottles different in shape and size are filled. In this example, concentrations of the hydrogen peroxide in the sample solutions were determined by using the concentration estimation equation, the concentrations were actually measured by using an established analytical method on the sample solutions, and then whether the measured concentrations are accurate or not was determined by comparing both concentrations.

(i) Formulation of Concentration Estimation Equation

Figure 3:
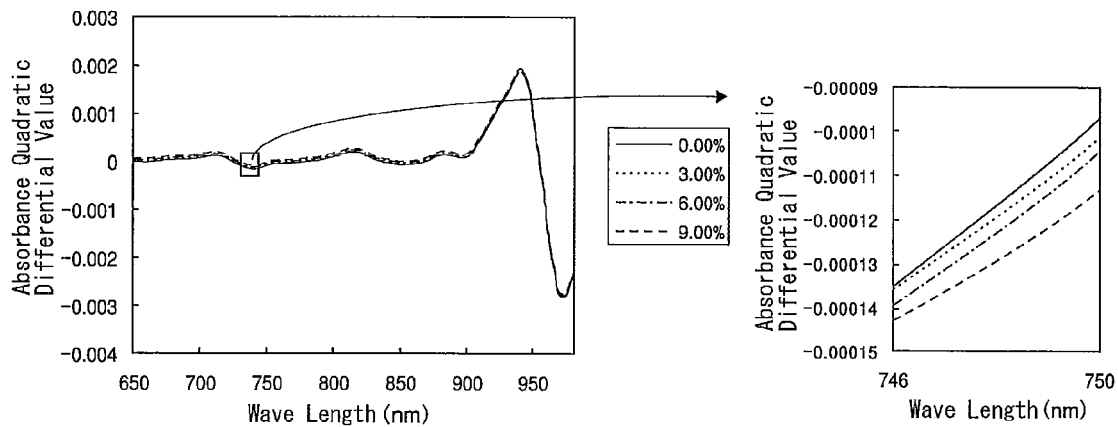
FIG. 3 is a graph showing results of quadratic differentiation of absorption spectra obtained in Example 1 of the invention.

Initially, a plurality of aqueous hydrogen peroxide solutions were prepared as samples, and then a near-infrared absorption spectrum of each sample was obtained. Next, the absorption spectra thus obtained were subjected to quadratic differentiation. FIG. 3 shows results of the quadratic differentiation of the absorption spectra obtained by using the samples with the concentrations of 0%, 3%, 6% and 9% and an enlarged view of a part of the result. Then, absorbance quadratic differential values at three wavelengths of 748 nm, 958 nm, 850 nm were determined. Thereafter, a following equation (3), another concentration estimation equation, was formulated by using the concentrations of the hydrogen peroxide in the aqueous hydrogen peroxide solutions and the determined absorbance quadratic differential values according to the foregoing procedure of the formulation of the concentration estimation equation.

$$C=5.18+1901000E_1+2660E_2+360000E_3 \quad (3)$$

wherein c is a concentration (an estimated value),
$E_1$, $E_2$ and $E_3$ are absorbance quadratic differential values at the wavelength of 748 nm, 958 nm, and 850 nm, respectively.

(ii) Measurement of Concentrations

To ascertain that the solution inspections can be conducted without being influenced by the shapes and sizes of the containers and the quantities of the liquids, PET containers different in shape and size, such as PET containers for tea, were prepared. Hydrogen peroxide solutions with concentrations of 0% to 10% by mass were prepared by using three methods described below.

(1) the concentration of each $H_2O_2$ was changed by adding different quantities of water to a fixed quantity of $H_2O_2$.
(2) the concentration of each $H_2O_2$ was changed by adding different quantities of $H_2O_2$ to a fixed quantity of water, and
(3) the concentration of each $H_2O_2$ was changed by changing a mixture ratio between the $H_2O_2$ and the $H_2O$ without changing their total quantity.

Then inspection samples were prepared by filling the PET containers with the solutions.

Then, absorption spectra of the samples were measured under same conditions as the conditions used in formulation of the concentration estimation equation. Thereafter, by subjecting the measured absorption spectra to quadratic differentiation, absorbance quadratic differential values at wavelengths of 748 nm, 958 nm and 850 nm were determined. Then, estimated values of the concentrations were calculated by substituting the determined absorbance quadratic differential values into Equation (3).

(iii) Results of Concentration Measurement and Results of Verification

The concentration of the hydrogen peroxide in each sample was actually measured by using an established analytical method. Then, the actual measured values obtained by the analysis were compared with the estimated values calculated by using the concentration estimation equation.

Figure 4:
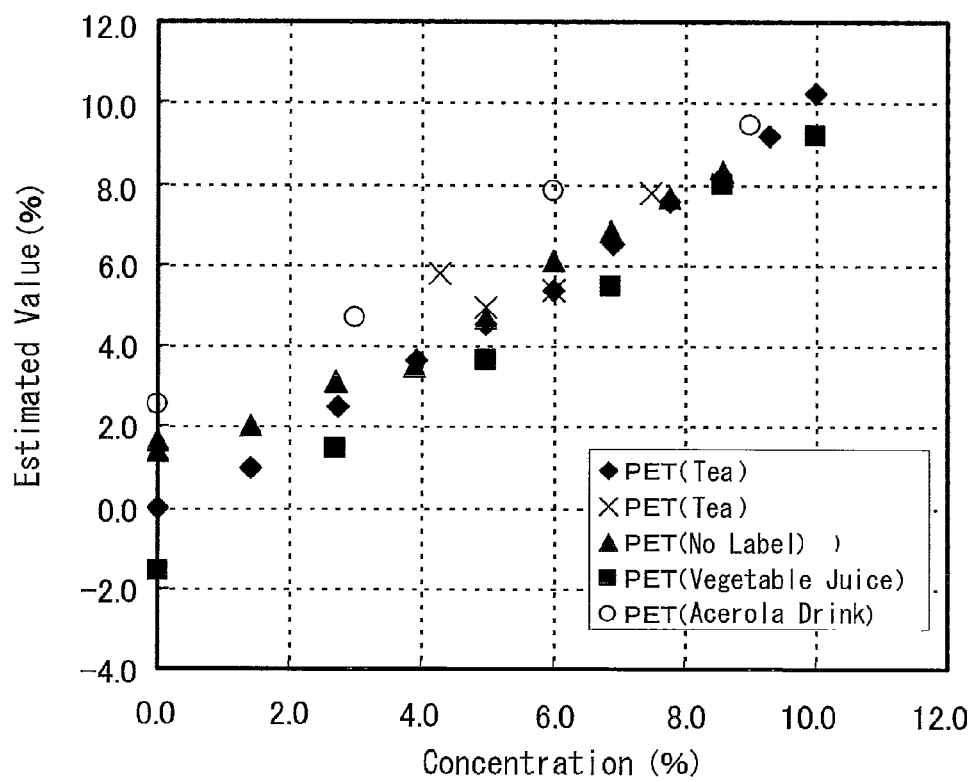
FIG. 4 is a graph showing a relation between estimated values and actually measured values of dangerous substance concentrations obtained in Example 1 of the invention.

FIG. 4 is a graph showing relation between the estimated values and the actually measured values of the concentrations of the dangerous substances; the figure also shows the containers and the measurement conditions used in the inspection. In FIG. 4, the vertical axis indicates the estimated values (the concentrations calculated by using the concentration estimation equation), and the horizontal axis indicates the concentrations actually measured by using the established analytical method. As shown in FIG. 4, the estimated values of the concentrations were in good agreement with the concentrations actually measured. From this example, it can be seen that even when containers are different in shape and size and liquids are different in quantity, a concentration of hydrogen peroxide can be measured correctly and accurately by using one concentration estimation equation.

EXAMPLE 2

This is an example of formulation of a concentration estimation equation about acetone solutions with which PET bottles are filled.

(i) Formulation of Concentration Estimation Equation

Figure 5:
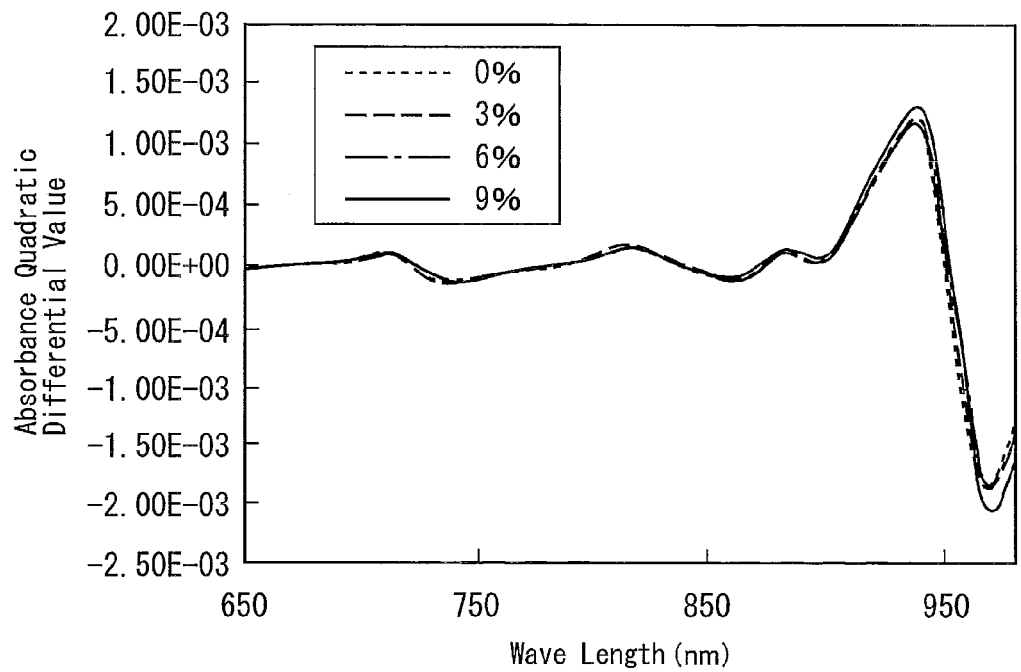
FIG. 5 is a graph showing results of quadratic differentiation of absorption spectra obtained in Example 2 of the invention.

By filling PET bottles with acetone solutions different in concentration, twelve samples were prepared. A near-infrared absorption spectrum was measured for each sample by using a same method as the method used in Example 1, following which the obtained absorption spectra were subjected to quadratic differentiation. Separately, concentration of the acetone in each sample was actually measured by using an established analytical method. FIG. 5 shows results of having subjected the absorption spectra of samples with the acetone concentrations of 0%, 3%, 6% and 9% to quadratic differentiation.

Next, wavelengths of 724 nm, 892 nm, and 850 nm were selected, and absorbance quadratic differential values at those wavelengths were determined from FIG. 5. Thereafter, a concentration estimation equation shown as a following equation (4) was formulated by using a same method as the method described in Example 1.

$$c=11.2+805000E_1-150000E_2-223000E_3 \quad (4)$$

wherein c is an estimated value of the concentration,
$E_1$, $E_2$ and $E_3$ are absorbance quadratic differential values at the wavelength of 724 nm, 892 nm and 850 nm, respectively.

(ii) Evaluation of Concentration Estimation Equation

Figure 6:
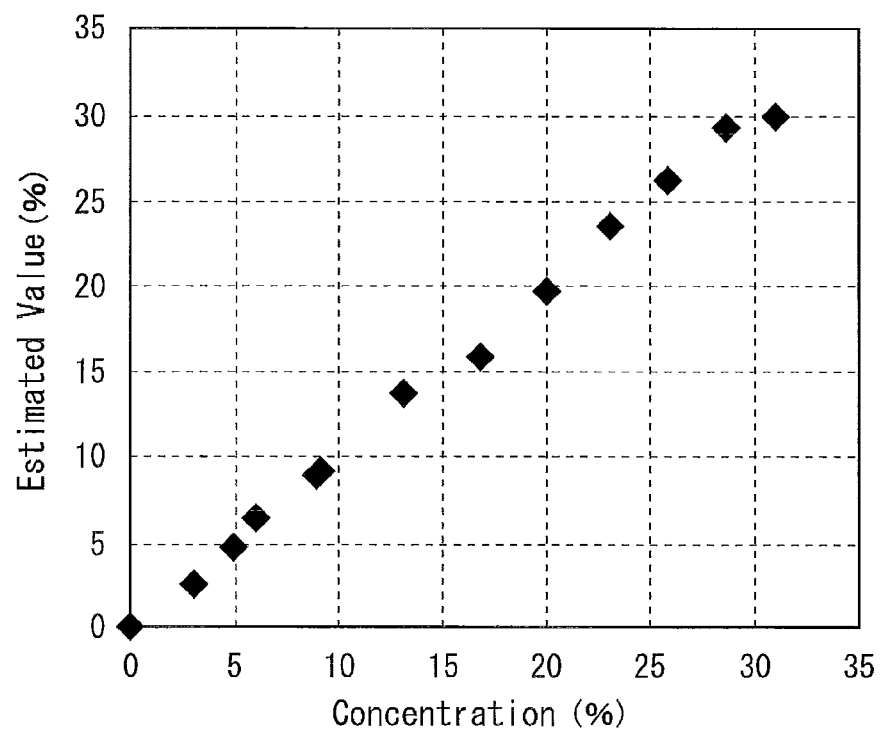
FIG. 6 is a graph showing a relation between estimated values and actually measured values of dangerous substance concentrations obtained in Example 2 of the invention.

FIG. 6 shows results of comparisons of the estimated values calculated by using the concentration estimation equation mentioned above and the actually measured concentrations regarding the twelve samples. In FIG. 6, the vertical axis indicates the estimated values of the concentrations, and the horizontal axis indicates the concentrations actually measured through the analysis. As shown in FIG. 6, relation between the estimated values for each sample and the concentrations actually measured through the analysis can be represented in the form of substantially one straight line with gradient of 1. Therefore, in this example as well, it can be seen that the concentration estimation equation with high accuracy is formulated.

DESCRIPTION OF THE REFERENCE NUMERALS 1 container
2 liquid
10 sensor head
11 irradiation unit
12 light reception unit
13, 14 optical fiber
15 near-infrared light
16 scattered near-infrared light
21 light source
22, 23 lens
24 prism
25 absorption spectrum
26 absorbance
27 PC

The invention claimed is:

1. A liquid inspection method for checking whether an explosive, a raw material for explosive, or an illicit drug is contained in a liquid with which an optically transparent container for a drink is filled, comprising:
a near-infrared irradiation step in which a substantially whole portion of the liquid is irradiated by an irradiation unit with near-infrared light having wavelengths of 650 to 1000 nm from outside the container;
a near-infrared light reception step in which the near-infrared light passed through the liquid or the near-infrared light scattered by the liquid is received by a light reception unit; and
an absorption spectrum analysis step in which an absorption spectrum of the received near-infrared light is analyzed,
wherein whether an explosive, a raw material for explosive, or an illicit material is contained in a liquid with which the container is filled is checked by analyzing the absorption spectrum,
the liquid is a drink which may contain the explosive, a raw material for an explosive or an illicit drug filled in the optically transparent container,
the irradiation unit and the light reception unit are integrated,
the near-infrared light is emitted by the irradiation unit into the container from a surface of the container to conduct the near-infrared irradiation step, and the near-infrared light scattered by the liquid is received through the surface of the container by the light reception unit to conduct the near-infrared light reception step.

2. The liquid inspection method according to claim 1, wherein identification of the kinds of the explosive, raw material for explosive, and/or illicit drug is conducted by analyzing the absorption spectrum.

3. The liquid inspection method according to claim 1 or claim 2, wherein absorbance at the predetermined wavelengths of an absorption spectrum analyzed at the absorption spectrum analysis step is substituted into a concentration estimation equation formulated based on absorption spectra analyzed by using a plurality of liquids that contain the explosive, the raw material for explosive, and/or the illicit drug with preset concentrations to measure a concentration of the explosive, the raw material for explosive, and/or the illicit drug.

4. The liquid inspection method according to claim 3, wherein the concentration estimation equation is formulated by conducting multiple regression analyses by using the absorbances at the wavelengths of the absorption spectra analyzed by using the liquids containing the explosive, the raw material for explosive, and/or the illicit drug with the preset concentrations.

5. The liquid inspection method according to claim 3, wherein an absorbance quadratic differential value at the predetermined wavelengths which is obtained by a quadratic differentiation for the absorption spectra is used as the absorbance.

6. The liquid inspection method according to claim 1, wherein the raw material for explosive is hydrogen peroxide.

7. The liquid inspection method according to claim 3, wherein regular products are used as the liquids containing the explosive, the raw material for explosive, and/or the illicit drug with the preset concentrations,
a concentration estimation equation is previously formulated for each of the regular products,
a regular product corresponding to the inspection object is identified by reading the product labeling mark put on the inspection object, and
the concentration of liquid explosive, raw material for explosive, and/or illicit drug in the inspection objects is measured by using the concentration estimation equation corresponding to the identified regular product, wherein
the regular product is control of a sample type to be tested.

8. A liquid inspection device for inspecting whether an explosive, a raw material for explosive, or an illicit drug is contained in a liquid with which an optically transparent container for a drink is filled, comprising:
a near-infrared light irradiation means for irradiating a substantially whole portion of the liquid with near-infrared light having wavelengths of 650 to 1000 nm from outside the container;
a near-infrared light reception means for receiving the near-infrared light passed through the liquid or the near-infrared light scattered by the liquid; and
an absorption spectrum analysis means for analyzing an absorption spectrum of the received near-infrared light,
wherein whether an explosive, a raw material for explosive, or an illicit drug is contained in the liquid with which the container is filled is inspected by analyzing the absorption spectrum, and
the liquid is a drink which may contain the explosive, a raw material for an explosive or an illicit drug filled in the optically transparent container,
the near-infrared light irradiation means and the near-infrared light reception means are integrated, and
the unit is disponed under the container so that the near-infrared light is emitted by the near-infrared light irradiation means into the container from a surface thereof and the near-infrared light scattered by the liquid is received through the surface of the container by the near-infrared light reception means.

9. The liquid inspection device according to claim 8, which further comprising a product labeling mark reading means for reading a product labeling mark put on a regular product, wherein i) said product labeling mark reading means identifies the regular product and the device, ii) identifies a previously formulated concentration estimation equation, and iii) compares the previously formulated equation with a concentration of an explosive, a raw material for explosive or the illicit drug in the liquid to be inspected.

10. The liquid inspection method according to claim 1, wherein
the irradiation unit is a white lamp.

11. The liquid inspection method according to claim 1, wherein
the container is shield from an extraneous light other than the near-infrared light.

12. The liquid inspection device according to claim 8, wherein
the near-infrared light irradiation means is a white lamp.

13. The liquid inspection device according to claim 8, further comprising a shield so that the container is shield by the shield from an extraneous light other than the near-infrared light.

14. The liquid inspection method according to claim 1, wherein the surface is a bottom of the container.

15. The liquid inspection method according to claim 8, wherein the surface is a bottom of the container.

* * * * *